US010918755B2

(12) United States Patent
Hitomi et al.

(10) Patent No.: US 10,918,755 B2
(45) Date of Patent: Feb. 16, 2021

(54) HOUSING APPARATUS

(71) Applicant: PHC HOLDINGS CORPORATION, Tokyo (JP)

(72) Inventors: Tsugumasa Hitomi, Gunma (JP); Manami Baba, Gunma (JP); Megumi Onda, Gunma (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 0 days.

(21) Appl. No.: 16/518,778

(22) Filed: Jul. 22, 2019

(65) Prior Publication Data

US 2019/0336634 A1    Nov. 7, 2019

Related U.S. Application Data

(63) Continuation of application No. PCT/JP2018/000069, filed on Jan. 5, 2018.

(30) Foreign Application Priority Data

Jan. 23, 2017  (JP) .............................. JP2017-009724
May 31, 2017  (JP) .............................. JP2017-108074

(51) Int. Cl.
  *A61L 2/26*    (2006.01)
  *A61L 2/10*    (2006.01)
  (Continued)

(52) U.S. Cl.
  CPC ................. *A61L 2/26* (2013.01); *A61L 2/10* (2013.01); *C12M 29/20* (2013.01); *C12M 37/00* (2013.01);
  (Continued)

(58) Field of Classification Search
  None
  See application file for complete search history.

(56) References Cited

U.S. PATENT DOCUMENTS 5,823,806 A * 10/1998 Nagase .................. H01R 13/44
                                                    439/140
6,089,887 A *  7/2000 Ozaki ................ H01R 33/0809
                                                    200/51.09
(Continued)

FOREIGN PATENT DOCUMENTS

JP    S59-042882 A    3/1984
JP    H04-169774 A    6/1992
(Continued)

OTHER PUBLICATIONS

International Search Report and Written Opinion issued in International Patent Application No. PCT/JP2018/000069, dated Apr. 3, 2018; with English translation.

*Primary Examiner* — Andrew Smyth
(74) *Attorney, Agent, or Firm* — McDermott Will and Emery LLP

(57) ABSTRACT

This accommodation device is for performing sterilization through irradiation with ultraviolet light. The device is provided with an ultraviolet light lamp for emitting ultraviolet light, electric wires for supplying power to the ultraviolet light lamp, socket parts for supporting the ultraviolet light lamp, and a housing in which the ultraviolet light lamp is disposed, wherein: the socket parts have formed therein first opening portions which are open to the inside of the housing, and second opening portions which are in fluid connection with the first opening portions and through which the electric wires pass; and the housing has formed therein third opening portions which guide the electric wires to the outside and which are in fluid connection with the second opening portions.

4 Claims, 4 Drawing Sheets

(51) Int. Cl.
*C12M 1/00* (2006.01)
*C12M 1/12* (2006.01)

(52) U.S. Cl.
CPC ...... *A61L 2202/11* (2013.01); *A61L 2202/122* (2013.01)

(56) References Cited

U.S. PATENT DOCUMENTS

| | | | | |
|---|---|---|---|---|
| 6,224,428 | B1* | 5/2001 | Chen | H01R 33/9655 439/188 |
| 6,325,668 | B1* | 12/2001 | Sato | H01R 33/9655 439/587 |
| 6,352,443 | B1* | 3/2002 | Takahashi | F21V 19/006 439/336 |
| 7,052,301 | B2* | 5/2006 | Garcia | H01R 33/09 362/249.14 |
| 2006/0198138 | A1* | 9/2006 | Seika | A47G 33/06 362/234 |
| 2010/0167383 | A1* | 7/2010 | Busujima | C12M 37/06 435/286.1 |
| 2010/0173401 | A1 | 7/2010 | Kobayashi et al. | |
| 2012/0140480 | A1* | 6/2012 | Taniuchi | F21V 23/006 362/296.01 |
| 2013/0322087 | A1* | 12/2013 | Tseng | F21V 19/0025 362/311.02 |
| 2017/0146217 | A1* | 5/2017 | McCracken, Jr. | F21V 17/005 |

FOREIGN PATENT DOCUMENTS

| | | |
|---|---|---|
| JP | H08-322552 A | 12/1996 |
| JP | 2009-014295 A | 1/2009 |
| JP | 2010-051184 A | 3/2010 |
| JP | 2010-051218 A | 3/2010 |

* cited by examiner

HOUSING APPARATUS

CROSS-REFERENCE OF RELATED APPLICATIONS

This application is the U.S. Continuation of International Patent Application No. PCT/JP2018/000069, filed on Jan. 5, 2018, which in turn claims the benefit of Japanese Application No. 2017-009724, filed on Jan. 23, 2017, and Japanese Patent Application No. 2017-108074, filed on May 31, 2017, the entire disclosures of which Applications are incorporated by reference herein.

TECHNICAL FIELD

The present invention relates to a housing apparatus that performs sterilization by irradiation with ultraviolet light.

BACKGROUND ART

In the related art, culture apparatuses for culturing cultures such as cells or microorganisms are widely used. Some culture apparatuses are provided with a heater or the like to adjust the temperature in the culture chamber. In addition, some apparatuses are provided with ultraviolet lamps to sterilize the culture chamber.

Patent Literature (hereinafter, abbreviated as PTL) 1 discloses a culture apparatus provided with an exhaust pipe for ventilating the culture chamber. In this culture apparatus, it is possible to prevent a gas generated by cell metabolism from accumulating in the culture chamber.

CITATION LIST

Patent Literature
  PTL 1
  Japanese Patent Application Laid-Open No. H08-322552

SUMMARY OF INVENTION

Technical Problem

However, since an exhaust pipe is added, the related art of PTL 1 described above has an increased number of parts and requires a space for providing the exhaust pipe in the culture apparatus.

In addition, when additionally providing an ultraviolet lamp in the culture apparatus, it is necessary to form an opening for passing the electric wire for supplying power to the ultraviolet lamp in addition to the opening for passing the exhaust pipe in the casing of the culture apparatus, so that the working is laborious.

An object of the present invention is to provide a housing apparatus that can easily form an exhaust passage for exhausting the gas in the casing, without increasing the number of parts and eliminate the need for a large installation space.

Solution to Problem

A housing apparatus of the present invention is a housing apparatus that performs sterilization by irradiation with ultraviolet light, the housing apparatus including: an ultraviolet lamp that radiates the ultraviolet light; an electric wire that supplies power to the ultraviolet lamp; a socket section that supports the ultraviolet lamp; and a casing inside of which the ultraviolet lamp is disposed, in which the socket section includes a first opening and a second opening, the first opening being opened toward an interior of the casing, the second opening being in fluid communication with the first opening and being an opening through which the electric wire passes, and in the casing, a third opening which guides the electric wire to outside is formed, the third opening being in fluid communication with the second opening.

Advantageous Effect of Invention

According to the present invention, it is possible to easily form an exhaust passage for exhausting the gas in the casing without increasing the number of parts and eliminate the need for a large installation space.

DESCRIPTION OF EMBODIMENTS

Hereinafter, embodiments of the present invention will be described in detail with reference to the drawings.

Figure 1:
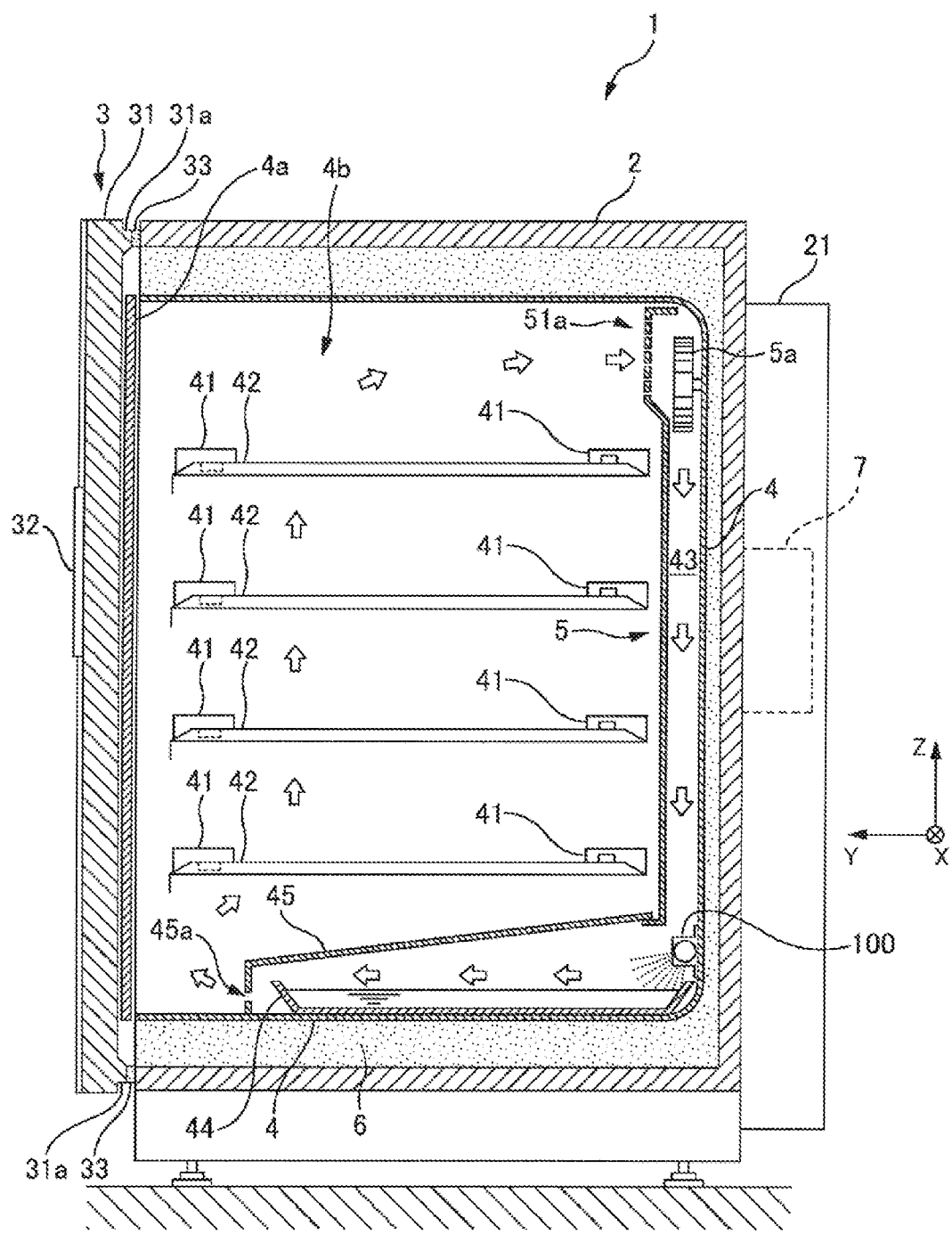
FIG. 1 is a cross-sectional side view illustrating an example of an overall structure of a culture apparatus according to the present embodiment.

First, an example of the overall structure of culture apparatus 1 according to the present embodiment will be described. FIG. 1 is a cross-sectional side view illustrating an example of an overall structure of culture apparatus 1 according to the present embodiment.

As illustrated in FIG. 1, culture apparatus 1 includes inner box 4, outer box 2, inner door 4a, outer door 3, and ultraviolet lamp 100. The structure around ultraviolet lamp 100 will be described with reference to FIG. 2 in detail later. Culture apparatus 1 is for culturing cultures such as cells and microorganisms in culture chamber 4b of inner box 4.

Inner box 4 is, for example, a substantially rectangular box made of stainless steel, and culture chamber 4b is formed inside thereof. Culture chamber 4b is partitioned in a vertical direction (Z-axis direction) by a plurality of shelves 42 for placing the cultures.

Shelves 42 include a plurality of holes (not illustrated) penetrating therethrough in a vertical direction, and are supported by a pair of shelf holders 41 provided in an interior of the two inner surfaces perpendicular to X-axis of inner box 4. Shelves 42 and shelf holders 41 are made, for example, of stainless steel.

Outer box 2 is, for example, a box made of stainless steel having a substantially similar shape to inner boxes 4, and houses inner boxes 4 in the interior thereof in a state of being insulated from the outside air. Provided between outer box 2 and inner boxes 4 is insulation material 6 for heat retention. Outer box 2, inner box 4, and insulation material 6 are casings of culture apparatus 1 the inside of which ultraviolet lamp 100 is disposed.

On an outer surface on a back side (negative direction side of Y-axis) of outer box 2, there are provided a sensor (not illustrated) for detecting a temperature in culture chamber 4b, a nozzle (not illustrated) for injecting gas such as carbon dioxide into culture chamber 4b, a sensor (not illustrated) for detecting a concentration of carbon dioxide in the interior of culture chamber 4b, and sensor box 7 having a heater (not illustrated) or the like.

The nozzle, the sensor or the like are, for example, attached to outer box 2 from the outer surface thereof on the back side of inner box 4 through a hole (not illustrated) formed on the outer surface on the back side of outer box 2. The outer surface of outer box 2 on the back side and sensor box 7 are covered with cover 21 having an insulation material (not illustrated) on an inner side thereof.

Inner door 4a is a flat-panel shaped door that enables opening and closing of the opening on the front side of inner box 4 (the positive direction side of Y-axis). Inner door 4a is, for example, formed of reinforce glass. When inner door 4a is closed, the interior of inner box 4 may be hermetically sealed by using a packing (not illustrated).

Outer door 3 is a door having a flat-panel shape that enables opening and closing of the opening of outer box 2 on the front side. Outer door 3 is formed, for example, of metal. Outer door 3 includes inside thereof door body 31 formed of a metal and provided on an inner side thereof with an insulation material (not illustrated) for heat retention and a heater (not illustrated) or the like, for adjusting the temperature in the interior of culture chamber 4b, and packing 33 attached to protruding part 31a opposing outer box 2.

Outer door 3 further includes control panel 32 on the front side of door body 31. Control panel 32 has components such as a keyboard (not illustrated) for inputting lighting duration of ultraviolet lamp 100 or the like, and a display (not illustrated) for displaying various information.

Ultraviolet lamp 100 kills bacteria contained in the air passing under duct 43 (the negative direction side of Z-axis) and the humidified water in humidification tray 44 arranged below duct 43, and is placed at a position where ultraviolet light can be radiated.

Here, duct 43 is composed of the back side wall of inner box 4 and wall plate 5 to form an air flow path therebetween. For example, wall plate 5 is made of stainless steel. Further, fan 5a (sirocco fan) is provided on the upper side (the positive direction side of Z-axis) in duct 43.

Humidification tray 44 is covered with cover 45 having hole 45a on the front side. For example, cover 45 is made of stainless steel.

Also, with fan 5a being rotated in a fixed direction, the air on the side of shelves 42 above culture chamber 4b flows into duct 43 through inlet port 51a as shown by the arrow, flows in duct 43 from the top to the bottom, and then flows forward on the surface of the humidified water. There, the humidified air passes through holes 45a of cover 45 to form an ascending air flow.

The air which has risen to the upper side of culture chamber 4b again flows into duct 43 through inlet port 51a. By such air circulation, inside culture chamber 4b is maintained at a substantially uniform temperature, humidity, and gas concentration such as carbon dioxide.

Further, ultraviolet lamp 100 is provided with an optical filter or the like to suppress generation of ultraviolet light having a wavelength of 200 nm or less. As a result, the generation of ozone from the gas in duct 43 (air, gas such as carbon dioxide, water vapor, and the like) is suppressed. In addition, the adverse effect of ozone on the culture in culture chamber 4b is also suppressed.

Figure 2:
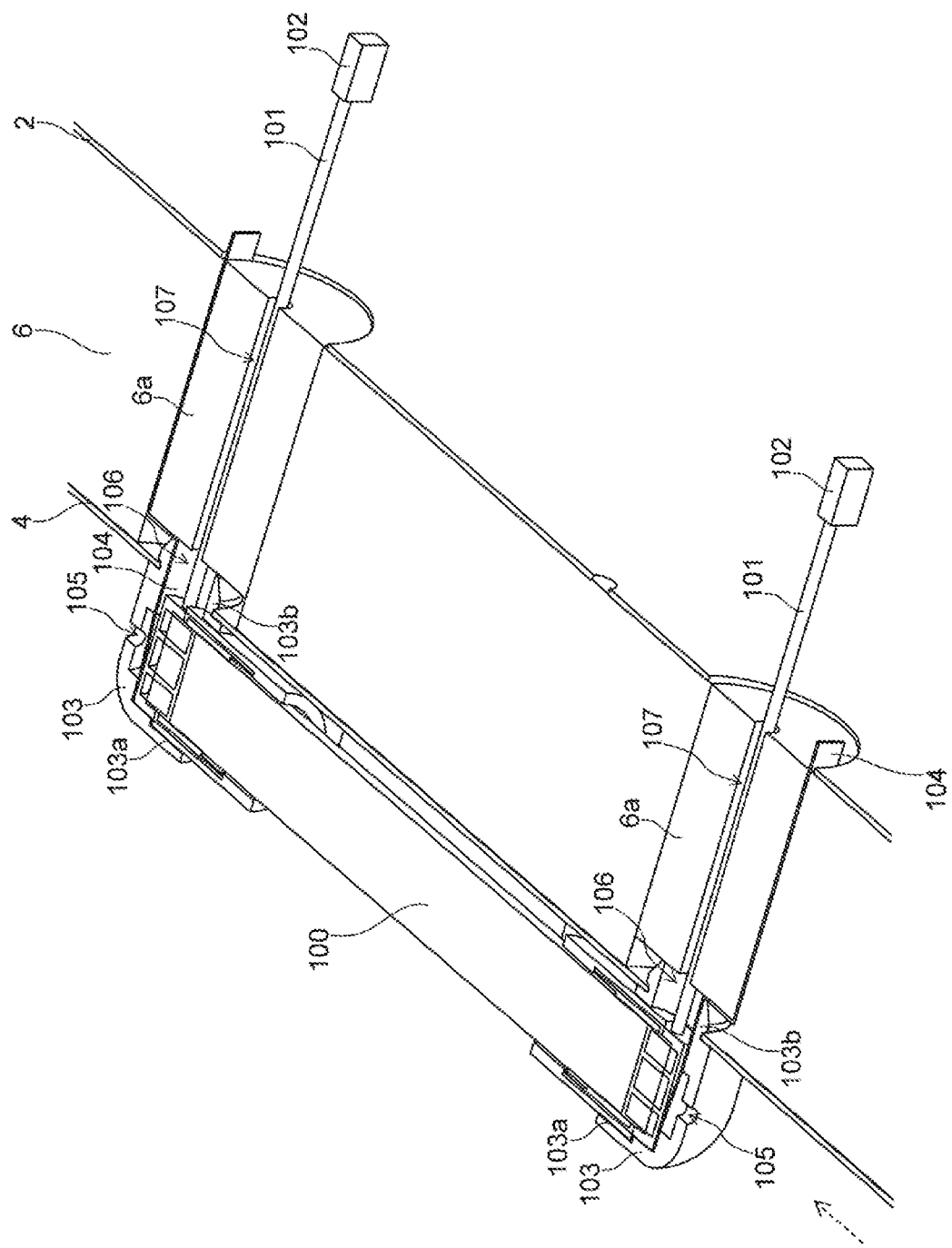
FIG. 2 is a cross-sectional plan view illustrating an example of an exhaust passage of the culture apparatus according to the present embodiment.

Next, an example of exhaust passage of the culture apparatus according to the present embodiment will be described. FIG. 2 is a cross-sectional plan view showing an example of exhaust passage of the culture apparatus according to the present embodiment.

As shown in FIG. 2, culture apparatus 1 includes electric wire 101, connector 102, socket section 103, and evaporation member 104 around ultraviolet lamp 100.

Electric wire 101 supplies power to ultraviolet lamp 100. Although electric wire 101 is drawn short in FIG. 2, the length of electric wire 101 may be longer. Also, FIG. 2 illustrates that one electric wire 101 is connected to each end of ultraviolet lamp 100, but two or more electric wires 101 may be connected to each end of ultraviolet lamp 100. Connector 102 is a component for connecting electric wire 101 to an electric circuit board (not illustrated).

Figure 3:
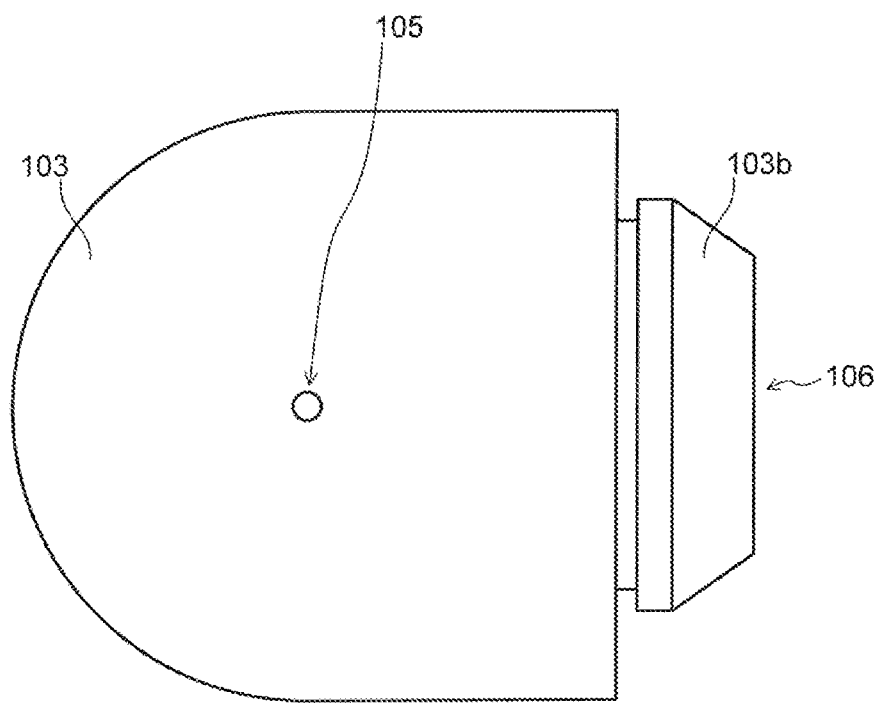
FIG. 3 is a side view illustrating an example of a socket section according to the present embodiment.

Socket section 103 is a component that supports ultraviolet lamp 100. FIG. 3 is a side view illustrating an example of socket section 103 according to the present embodiment. The side view in FIG. 3 is a view of socket section 103 as viewed from the direction of dotted arrow in FIG. 2.

Socket section 103 is an elastic body having an L shape, and ultraviolet lamp 100 is fitted in recessed part 103a at one end, and protruding part 103b at the other end is fitted in the opening of inner box 4. Accordingly, ultraviolet lamp 100 is supported by socket section 103, and socket section 103 is fixed to a casing (hereinafter referred to simply as casing) composed of outer box 2, inner box 4, and insulation material 6.

Socket section 103 is provided with, as shown in FIGS. 2 and 3, first opening 105 which is opened toward an interior of the casing (the interior of inner box 4) and second opening 106 in fluid communication with first opening 105 and through which electric wire 101 passes.

The casing is provided with third opening 107 for guiding electric wire 101 to the outside and in fluid communication with second opening 106. First opening 105, second opening 106, and third opening 107 form an exhaust passage for exhausting the gas inside the casing to the outside.

That is, when the pressure of the gas inside the casing is higher than the pressure of the gas outside the casing, the gas inside the casing is exhausted to the outside via first opening 105, second opening 106, and third opening 107.

Evaporation member 104 is a member having one end disposed in first opening 105 and the other end disposed at the exterior of the casing, and causing water absorbed to evaporate from the one end from the other end. Evaporation member 104 may be made of paper, cloth or the like, and may be made of an inorganic or organic material as long as it causes capillary action to water.

Here, when replacing ultraviolet lamp 100, part 6a of the insulation material is removed for easy replacement. Evaporation member 104 is disposed utilizing a gap between part 6a of the insulation material and the other part. In addition, since evaporation member 104 has air permeability, even if evaporation member 104 is disposed in first opening 105 and second opening 106 as shown in FIG. 2, exhaust of gas through the above-described exhaust route is not hindered.

Second opening 106 and third opening 107 are essentially required openings to pass electric wire 101. In the present embodiment, by utilizing these openings, exhaust passages can be formed only by forming first opening 105 in socket section 103.

Therefore, the number of parts does not increase to form the exhaust passage. Also, since there is no need to add an exhaust pipe to form the exhaust passage, the installation space for installing the exhaust pipe is also unnecessary. Furthermore, the exhaust passage can be easily formed.

Further, by providing evaporation member 104 described above, water accumulated in first opening 105, second opening 106, and third opening 107 can be removed. For example, even if the condensation is generated in socket section 103 by contact with the outside air, the water can be absorbed and removed by evaporation member 104, leaving the water to evaporate outside the casing. As a result, it is possible to suppress the reproduction of various bacteria.

In the above embodiment, one end of evaporation member 104 is disposed in first opening 105 and other end is disposed at the exterior of the casing. However, one end of evaporation member 104 is disposed in second opening 106, and the other end may be disposed at the exterior of the casing.

Figure 4:
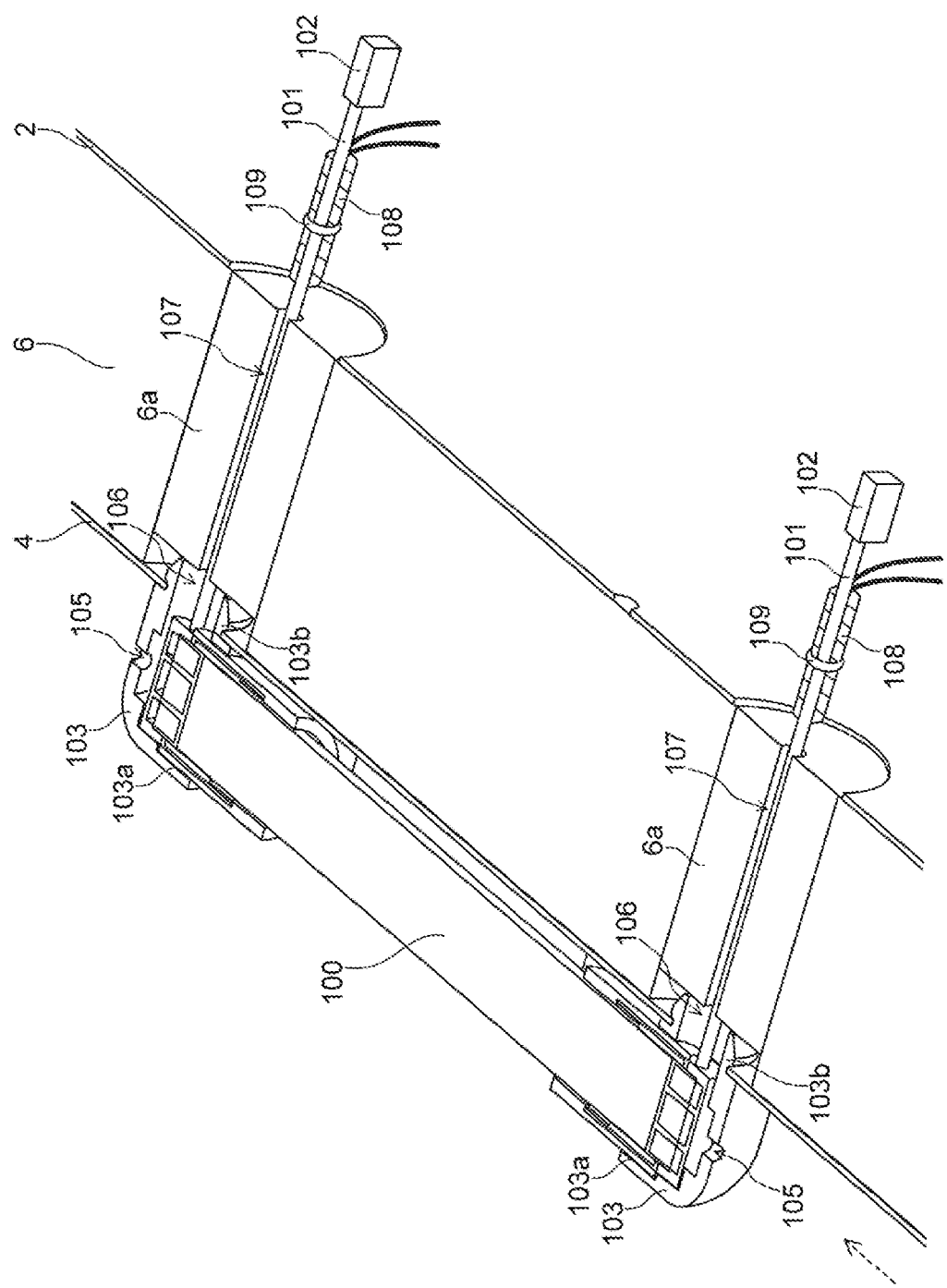
FIG. 4 illustrates an example of a heating section provided in an electric wire which passes the exhaust passage of the culture apparatus which concerns on the present embodiment.

Also, instead of evaporation member 104, heating section 108 may be provided to evaporate the water. FIG. 4 illustrates an example of heating section 108 provided on an electric wire passing through the exhaust passage of the culture apparatus according to the present embodiment. FIG. 4 illustrates heating section 108 tied to electric wire 101 using binding band 109.

Heating section 108 is a heater that generates heat. For example, heating section 108 is a heater that generates heat by means of current flowing through the resistor. Also, heating section 108 is provided at the exterior of the casing. Also, heating section 108 is provided to contact electric wire 101 over a predetermined range.

Heating section 108 is in contact with electric wire 101 over a predetermined range, and heating section 108 heats electric wire 101. This heat is transmitted to socket section 103 and part 6a of the insulation material, and socket section 103 and part 6a of the insulation material are heated.

Therefore, the water accumulated in first opening 105 and second opening 106 of socket section 103 can be evaporated. Also, water accumulated in third opening 107 of part 6a of the insulation material can be evaporated. Heating section 108 may be provided together with evaporation member 104.

In the above embodiment, culture apparatus 1 for culturing the cultures housed in the casing and sterilization by irradiation with ultraviolet light has been described. However, the present invention is not limited to such culture apparatus 1, and may be applied to a storage device that stores an object in a casing.

The disclosures of the specification, drawings and abstract included in Japanese Patent Application No. 2017-009724 filed on Jan. 23, 2017 and Japanese Patent Application No. 2017-108074 filed on May 31, 2017 are all incorporated herein by reference.

INDUSTRIAL APPLICABILITY

A housing apparatus according to the present invention is suitable for use in a housing apparatus that performs sterilization by irradiation with ultraviolet light.

REFERENCE SIGNS LIST

1 Culture apparatus
2 Outer box
3 Outer door
4 Inner box
4a Inner door
4b Culture chamber
5 Wall plate
5a Fan
6 Insulation material
7 Sensor box
21 Cover
31 Door body
31a Protruding part
32 Control panel
33 Packing
41 Shelf holder
42 Shelf
43 Duct
44 Humidification tray
45 Cover
45a Hole
51a Inlet port
100 Ultraviolet lamp
101 Electric wire
102 Connector
103 Socket section
103a Recessed part
103b Protruding part
104 Evaporation member
105 First opening
106 Second opening
107 Third opening
108 Heating section
109 Binding band

The invention claimed is:

1. A housing apparatus for sterilization by irradiation with UV light, the housing apparatus comprising:
a UV lamp that radiates the UV light;
an electric wire that supplies power to the UV lamp;
a socket section that supports the UV lamp;
a casing insulated from outside air and inside of which the UV lamp is disposed, wherein
the socket section includes a first opening and a second opening, the first opening being opened toward an interior of the casing, the second opening being in fluid communication with the first opening and being an opening through which the electric wire passes,
the socket section further includes a recessed part that extends axially in a first direction and a protruding part that extends axially in a second direction transverse to the first direction, the recessed part includes the UV lamp, and the protruding part includes the second opening and is received within the casing, and
the casing includes a third opening which guides the electric wire to outside, the third opening being in fluid communication with the second opening; and
a heating section located exterior of the casing,
wherein the heating section at least partially encloses a predetermined length of the electric wire and is configured to heat the electric wire.

2. The housing apparatus according to claim 1, wherein the third opening is an exhaust passage for exhausting gas in the interior of the casing to an exterior of the casing.

3. The housing apparatus according to claim 1, further comprising an evaporation member including one end disposed in the first opening or the second opening and another end disposed at the exterior of the casing, the evaporation member causing water absorbed from the one end to evaporate from the other end.

4. The housing apparatus according to claim 1, wherein a part of the casing in which the third opening is formed is removable from another part of the casing.

* * * * *